ns Patent [19]

United States Patent [19]

Braid

[11] Patent Number: 4,519,928
[45] Date of Patent: May 28, 1985

[54] LUBRICANT COMPOSITIONS CONTAINING N-TERTIARY ALKYL BENZOTRIAZOLES

[75] Inventor: Milton Braid, Westmont, N.J.

[73] Assignee: Mobil Oil Corporation, New York, N.Y.

[21] Appl. No.: 295,918

[22] Filed: Aug. 24, 1981

Related U.S. Application Data

[63] Continuation of Ser. No. 115,521, Jan. 25, 1980, abandoned, which is a continuation of Ser. No. 938,608, Aug. 31, 1978, abandoned.

[51] Int. Cl.$^3$ ............................................... C10M 1/32
[52] U.S. Cl. ...................................................... 252/50
[58] Field of Search .......................................... 252/50

[56] References Cited

U.S. PATENT DOCUMENTS

| 3,413,227 | 11/1968 | Howard et al. | 252/50 X |
| 3,597,353 | 8/1971 | Randell et al. | 252/50 |
| 3,849,433 | 11/1974 | Butula | 252/50 X |
| 4,060,491 | 11/1977 | Bridger et al. | 252/50 X |
| 4,115,288 | 9/1978 | Schmitt | 252/50 |

FOREIGN PATENT DOCUMENTS

| 1180385 | 2/1970 | United Kingdom | 252/50 |
| 1226100 | 3/1971 | United Kingdom | 252/50 |

*Primary Examiner*—Andrew H. Metz
*Attorney, Agent, or Firm*—Alexander J. McKillop; Michael G. Gilman; Howard M. Flournoy

[57] ABSTRACT

Lubricant compositions containing oleaginous materials and, in amounts sufficient to impart oxidation, and corrosion resistance properties thereto, N-t-alkylated benzotriazoles.

6 Claims, No Drawings

LUBRICANT COMPOSITIONS CONTAINING N-TERTIARY ALKYL BENZOTRIAZOLES

This is a continuation of now abandoned application Ser. No. 115,521, filed Jan. 25, 1980, which is a continuation of now abandoned application Ser. No. 938,608, filed Aug. 31, 1978.

BACKGROUND OF THE INVENTION

1. Field of the Invention

The invention relates to oleaginous compositions normally susceptible to oxidative deterioration and metal corrosion. In particular, the invention relates to compositions such as mineral and synthetic lubricating oils, gear oils, transmission fluids, greases, and other oleaginous compositions normally requiring the presence of antioxidants or anticorrosion additives.

2. Description of the Prior Art

Prior to the present invention, triazoles have been employed in lubricant compositions as metal deactivators. For example, U.S. Pat. No. 3,597,353 of Randell et al. discloses the use of 4,5,6,7-tetrahydrobenzotriazole as a metal deactivating additive for natural and synthetic lubricants. Similarly, U.S. Pat. No. 3,413,227 of Howard et al. teaches that an alkyl-substituted benzotriazole where the alkyl group contains from 2 to 20 carbon atoms can be used as a corrosion or tarnish inhibitor.

Bridger et al., in U.S. Pat. No. 4,060,491, discloses utilizing 5-alkyl benzotriazole, in which the alkyl group contains from 4 to 16 carbon atoms, in a method for reducing wear between moving steel-on-steel surfaces.

In U.S. Pat. No. 3,788,993 of Andress, it is taught that benzotriazoles react with alkyl- or alkenylsuccinic anhydrides to form reaction products which impart corrosion inhibiting properties to lubricating oils.

Nnadi et al., in U.S. Pat. No. 4,048,082, discloses that esters of adducts of benzotriazole and unsaturated dicarboxylic acids or anhydrides thereof impart anti-rust properties to organic compositions.

None of the prior art patents disclose the N-t-alkylated benzotriazoles of the present invention.

SUMMARY OF THE INVENTION

It has now been found that N-t-alkylated benzotriazoles, having the formula:

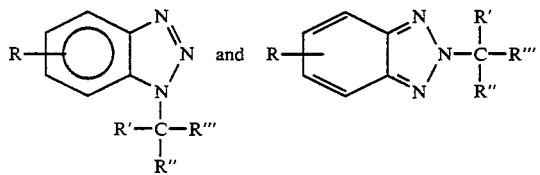

where R is hydrogen or a hydrocarbyl group containing from 1 to about 12 carbon atoms, $R'$ and $R''$ are alkyl groups containing from 1 to about 4 carbon atoms in any isomeric arrangement, and $R'''$ is an alkyl group containing from 1 to about 12 carbon atoms in any isomeric arrangement, impart antioxidation and metal corrosion prevention properties to the lubricant compositions to which they are added.

Referring to the above formulae, the preferred N-t-alkylated benzotriazoles are those in which R is hydrogen or an alkyl group containing from 1 to about 8 carbon atoms, $R'$ and $R''$ are alkyl groups containing from 1 to about 3 carbon atoms and $R'''$ is an alkyl group containing from 1 to about 8 carbon atoms.

Particularly preferred are those N-t-alkylated benzotriazoles in which:

R is hydrogen or a methyl group, $R'$ and $R''$ are methyl groups and $R'''$ is a dimethylpropyl group.

In general, the N-t-alkylated benzotriazoles utilized in the compositions of the present invention may be produced by reacting, in the presence of an acidic alkylation catalyst, a benzotriazole compound with an olefin in which at least one of the unsaturated carbon atoms is substituted by two alkyl groups.

The benzotriazole compounds which are used to form the N-t-alkylated benzotriazoles utilized in the compositions of the present invention have the formula:

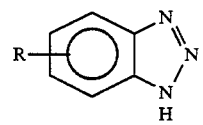

where R is hydrogen or hydrocarbyl containing from 1 to about 12 carbon atoms, and preferably is hydrogen or an alkyl group containing from 1 to about 8 carbon atoms. Particularly preferred are benzotriazole and toluotriazole.

The olefinic compounds which are used to form the N-t-alkylated benzotriazoles of the present invention are represented by the formula:

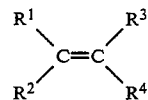

where $R^1$, $R^2$, $R^3$ and $R^4$ may be hydrogen or an alkyl group, however, at least either $R^1$ and $R^2$ or $R^3$ and $R^4$ must be alkyl. Olefins of the above formula and containing from 4 to about 20 carbon atoms are utilized to form the N-t-alkylated benzotriazoles of the present invention. Of these, olefins containing from 4 to about 16 carbon atoms are preferred, with olefins containing from 4 to about 8 carbon atoms particularly preferred.

The N-t-alkylated benzotriazole compound utilized in the lubricant compositions of the present invention are formed by reacting the benzotriazole compound with the olefin in proportions, expressed as molar ratios of benzotriazole compound to olefin, of from 1:0.5 to about 1:4, with from about 1:1 to about 1:3 being preferred.

Temperatures from about 5° C. to about 150° C., with from about 80° C. to about 140° C. being preferred, are utilized. In general, the reactants are contacted for about 0.5 to about 22 hours, with from about 2 to about 14 hrs. being preferred. As those of skill in the art are aware, the particular reaction times utilized depend on the temperature and the reactants employed. Thus, at higher temperatures, the reaction time may be shorter than the time at lower temperatures for a given pair of reactants.

Solvents such as pentane, cyclohexane, hexane, heptane, octane, nitrobenzene, trifluoromethyl benzene, perfluorobenzene and the like may be utilized.

The reaction is catalyzed by known acidic alkylation catalysts, such as $AlCl_3$, $SnCl_4$, $AlCl_3$-$SnCl_4$, $BF_3$, $BF_3$ etherate, sulfuric acid, phosphoric acid, polyphosphoric acid, methanesulfonic acid.

The N-t-alkylated benzotriazole reaction products may be used in the lubricant compositions of the present invention in their entirety. Alternatively, it has been found that the products can be fractionated by any method and the fractions utilized in the lubricant composition. Particularly, the reaction product can be fractionated by distillation, filtration, crystallization, partial freezing, chromotography or extraction with various solvents such as petroleum ether, cyclohexane, ether, acetone, or ethyl acetate.

Of particular significance, in accordance with the present invention, is the ability to improve the resistance to oxidation and corrosion of oleaginous materials such as lubricating media which may comprise liquid oils, in the form of either a mineral oil or a synthetic oil, or in the form of a grease in which any of the aforementioned oils are employed as a vehicle. In general, mineral oils, both paraffinic, naphthenic, aromatic, and mixtures thereof, employed as the lubricant, or grease vehicle, may be of any suitable lubricating viscosity range, as for example from about 45 SSU at 100° F. to about 6,000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quality of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl)ether, phenoxy phenylethers.

It is to be understood, however, that the compositions contemplated herein can also contain other materials. For example, corrosion inhibitors, extreme pressure agents, viscosity index agents, co-antioxidants, antiwear agents and the like can be used. These materials do not detract from the value of the compositions of this invenion, rather these materials serve to impart their customary properties to the particular compositions in which they are incorporated.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmission are defined in the ASTM Research Report D-2: RR 1005 on "Automatic Transmission Fluid/Power Transmission Fluid Property and Performance Definitions." Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

In general, the N-t-alkylated benzotriazoles of the present invention may be employed in any amount which is effective for imparting the desired degree of oxidation improvement or copper corrosion prevention. In many applications, however, the adduct is effectively employed in amounts from 0.01 to 10% by weight, and preferably from about 0.1 to 5% of the total weight of the composition.

DESCRIPTION OF SPECIFIC EMBODIMENTS

The following examples and comparative data will serve to illustrate the N-t-alkylated benzotriazole containing composition of the present invention, and the marked improvement in antioxidant and antirust properties of oleaginous materials containing said adducts. It will be understood, however, that it is not intended that the invention be limited to the particular compositions containing those adducts described herein. Various modifications of those adducts and compositions can be employed, as will be readily apparent to those skilled in the art.

EXAMPLE 1

Alkylation of Benzotriazole with Diisobutylene, Aluminum Chloride Catalyst

To benzotriazole (100 g.) melted, heated to 130° C. and stirred there was added aluminum chloride (0.1 g.) and the addition of diisobutylene drop by drop was begun. As the reaction mixture was cooled to 100° C. by refluxing olefin, addition was discontinued until consumption by alkylation allowed the temperature to rise to 120° C. where addition was resumed. This procedure was continued for 11 hrs. during which a total of 90 g. of diisobutylene was added. The reaction mixture was cooled, treated with water, extracted with benzene and filtered to remove solids. The benzene portion was separated, dried and stripped of solvent by rotary evaporation. The product N-tert-octylbenzotriazole was obtained as a tan semi-solid residue.

EXAMPLE 2

Alkylation of Benzotriazole with Diisobutylene, Aluminum Chloride-Stannic Chloride Catalyst To benzotriazole (100 g.) heated while stirring at 130° C., diisobutylene was added drop by drop until the refluxing olefin lowered the reaction mixture temperature to 120° C. There was no indication by gas chromatography that alkylation had occurred. To the reaction mixture a catalyst amount of aluminum chloride (0.1 g.) was added, the temperature was raised to 125° C. and addition of the olefin was resumed. After 5 hr. during which the addition was halted when the reaction temperature fell to 120° C. and resumed when consumption of the olefin raised the temperature to 128° C., substantial product peaks were observed by gas chromatography. To the reaction mixture stannic chloride (0.1 g.) was added and the intermittent addition of diisobutylene was described above with an additional 0.1 g. of aluminum chloride and 0.1 g. of stannic chloride added after 6.25 hr. and 7.25 hr., respectively. After a total reaction time of about 18 hr., a total of 100 g. of diisobutylene had been added. The reaction mixture was washed with water and extracted with benzene. The extract was dried and stripped of solvent and unreacted olefin by rotary evaporation. The residue, a mixture of solids and liquid, was separated. The oil fraction was tested without further purification. The solids were recrystallized from 2,2,4-trimethylpentane (isooctane) to obtain a white crystalline product, m.p. 62°–63° C.

EXAMPLE 3

Alkylation of Benzotriazole with Diisobutylene, Stannic Chloride-Aluminum Chloride Catalyst As in Examples 1 and 2, diisobutylene was added intermittently to benzotriazole (100 g.) containing stannic chloride (0.1 g.) for 2 hr., additional stannic chloride (0.2 g.) was: added and addition of the olefin was continued for 7 hr. with the reaction mixture temperature ranging from 130°–155° C. Aluminum chloride (0.1 g.) was added and the olefin addition was continued for 7 hr. at 150°–155° C. More than 70 g. of diisobutylene had been added to the reaction mixture during the total reaction time. The reaction mixture was washed with water and extracted with benzene. The extract was dried and stripped of solvent and unreacted olefin to leave the alkylated benzotriazole product as a mixture of solids and oils. The solids were removed by filtration and were used without further purification in lubricant compositions.

The N-t-alkylated benzotriazole compounds produced in the above examples were then tested for oxidation inhibition and copper corrosion prevention activity.

For the oxidation test, the adducts were blended into a neutral solvent refined mineral base oil having a viscosity at 100° F. of 130 SUS. The oils were then subjected to a stream of air at the rate of 5 liters per hour at a temperature of 325° F. for 40 hours in the presence of metals having prooxidant properties: iron, copper, lead and aluminum. The lead sample has been weighed before and after the test, since lead is one of the metals more susceptible to corrosion by oxidation. The test measurements are: change in acidity or neutralization number as measured by ASTM D-974, change in kinematic viscosity at 210° F., lead loss in milligrams and sludge. Results of the test are presented in Table 1.

TABLE 1

| CATALYTIC OXIDATION TEST 325° F., 40 HRS. | | | | |
|---|---|---|---|---|
| Base Oil | Δ NN | Δ KV | Pb loss, mg | Sludge |
| Base Oil without additives | 17 | 334 | 66 | Heavy |
| Product of Example 1 | | | | |
| Base Oil + 2 wt. % Product | 18.4 | 284 | 142 | Moderate |
| Base Oil + 1 wt. % Product | 18.8 | 197 | 50.7 | Light |
| Base Oil + 0.5 wt. % Product | 22.3 | 185 | 80.9 | Light |
| Product of Example 2 - Oil Fraction | | | | |
| Base Oil + 1 wt. % Product | 18.2 | 292 | 61.9 | Moderate |
| Base Oil + 0.5 wt. % Product | 21.2 | 193 | 47.8 | Moderate |
| Base Oil + 0.25 wt. % Product | 24.4 | 208 | 53.7 | Moderate |
| Product of Example 2 - Solid Fraction | | | | |
| Base Oil + 2 wt. % Product | 22.1 | 165 | 57.4 | Light |
| Base Oil + 1 wt. % Product | 15.9 | 96 | 26.3 | Moderate |
| Base Oil + 0.5 wt. % Product | 20.9 | 165 | 24.3 | Moderate |
| Product of Example 3 - Solid Fraction | | | | |
| Base Oil + 2 wt. % Product | 16.7 | 238 | 78.9 | Moderate |
| Base Oil + 1 wt. % Product | 15.8 | 220 | 82.5 | Light |
| Base Oil + 0.5 wt. % Product | 19.5 | 103 | 67.8 | Light |

As shown by the data presented in Table 1, the oxidative stability of the base oil is markedly improved by the addition of the additives of the present invention.

For the copper corrosion test, the products of Example 1, Example 2 (solid fraction) and Example 3 (solid fraction) were blended into a refined mineral base oil which contained 3% sulfurized isobutylene. The blends were then evaluated in the ASTM D130 test. In general, the test involves immersing a polished copper strip in the oil blend and heating at 212° F. for 6 hours. At the end of this period the strip was removed, washed, and compared with ASTM Copper Strip Corrosion Standards. The results are presented in Table 2.

TABLE 2

| ASTM D-130 Copper Corrosion Test | |
|---|---|
|  | Rating |
| Base Oil alone | 3B |
| Base Oil + 0.5 wt. % product of Example 1 | 1B |
| Base Oil + .25 wt. % product of Example 1 | 1B |
| Base Oil + 0.5 wt. % product of Example 2 (solid fraction) | 3B |
| Base Oil + 0.5 wt. % product of Example 3 (solid fraction) | 2C |

A rating of 1A or 1B denotes a slight tarnish, a rating of 2A, 2B, 2C, 2D, and 2E denotes a moderate tarnish; a rating of 3A or 3B denotes a dark tarnish and a rating of 4A, 4B, or 4C denotes severe corrosion.

The results presented in Table 2 indicate the efficacy of the adducts of the present invention in reducing copper corrosion.

I claim:

1. A lubricant composition which comprises a major amount of an oil of lubricating viscosity and a minor amount, of at least about 1 weight percent based on the total weight of the composition, effective to impart antioxidative and metal corrosion prevention properties thereto, of N-t-alkylated benzotriazoles, having the formula:

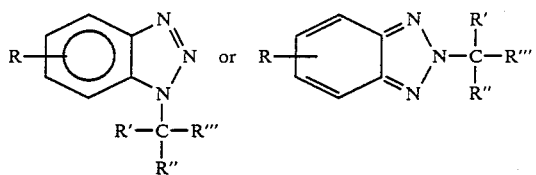

where R is hydrogen or a hydrocarbyl group containing from 1 to about 12 carbon atoms, R' and R" are alkyl groups containing from 1 to about 4 carbon atoms, and R'" is an alkyl group containing from 1 to about 12 carbon atoms.

2. The composition of claim 1 wherein R is hydrogen or an alkyl group containing from 1 to about 8 carbon atoms, R' and R" are alkyl groups containing from 1 to about 3 carbon atoms, and R'" is an alkyl group containing from 1 to about 8 carbon atoms.

3. The composition of claim 1 wherein R is hydrogen or a methyl group, R' and R" are methyl groups and R'" is a dimethylpropyl group.

4. The composition of claim 1 wherein said lubricant is selected from the group consisting of mineral oils, synthetic oils and greases thereof.

5. The composition of claim 1 wherein said N-t-alkylated benzotriazole is present in an amount from about 1 to about 10% by weight of the total composition.

6. The composition of claim 1 wherein said N-t-alkylated benzotriazole is present in an amount from about 1 to 5% by weight of the total composition.

* * * * *